(12) United States Patent
Ito et al.

(10) Patent No.: US 9,618,670 B2
(45) Date of Patent: Apr. 11, 2017

(54) LIGHT SOURCE APPARATUS

(71) Applicant: OLYMPUS CORPORATION, Tokyo (JP)

(72) Inventors: Takeshi Ito, Hino (JP); Eiji Yamamoto, Musashimurayama (JP); Masahiro Nishio, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 115 days.

(21) Appl. No.: 14/170,992

(22) Filed: Feb. 3, 2014

(65) Prior Publication Data

US 2014/0146559 A1    May 29, 2014

Related U.S. Application Data

(63) Continuation of application No. PCT/JP2012/069480, filed on Jul. 31, 2012.

(30) Foreign Application Priority Data

Aug. 2, 2011    (JP) .................. 2011-169506

(51) Int. Cl.
*G02B 6/36* (2006.01)
*F21V 8/00* (2006.01)
(Continued)

(52) U.S. Cl.
CPC .............. *G02B 6/0005* (2013.01); *A61B 1/05* (2013.01); *A61B 1/0653* (2013.01);
(Continued)

(58) Field of Classification Search
CPC ..... G02B 6/3898; G02B 6/3851; G02B 6/387
See application file for complete search history.

(56) References Cited

U.S. PATENT DOCUMENTS 4,140,365 A * 2/1979 Burger ................. G02B 6/3825
                                                           385/72
4,327,964 A * 5/1982 Haesly ................. G02B 6/3865
                                                           29/453
(Continued)

FOREIGN PATENT DOCUMENTS

EP    1 867 272 A1    12/2007
JP    1-164406 U    11/1989
(Continued)

OTHER PUBLICATIONS

Japanese Office Action dated May 12, 2015 from related Japanese Application No. 2011-169506, together with an English language translation.
(Continued)

*Primary Examiner* — Rhonda Peace
(74) *Attorney, Agent, or Firm* — Scully, Scott, Murphy & Presser, P.C.

(57) ABSTRACT

A light source apparatus includes: a primary light source module including a primary light source configured to emit primary light; a light conversion module including a light conversion unit configured to convert optical properties of the primary light and to generate secondary light; a light guide path, arranged between the primary light source module and the light conversion module, configured to guide the primary light to the light conversion module from the primary light source module; a first connecting portion configured to connect detachably the light conversion module with the light guide path; and a second connecting portion configured to connect detachably the primary light source module with the light guide path.

43 Claims, 7 Drawing Sheets (51) Int. Cl.
  A61B 1/05    (2006.01)
  A61B 1/06    (2006.01)
  G02B 23/24   (2006.01)
  F21V 31/00   (2006.01)
(52) U.S. Cl.
  CPC ............ *A61B 1/0669* (2013.01); *F21V 31/00* (2013.01); *G02B 23/2469* (2013.01)

(56) References Cited

U.S. PATENT DOCUMENTS

| | | | | |
|---|---|---|---|---|
| 4,421,383 A * | 12/1983 | Carlsen | ................... | G02B 6/32 385/72 |
| 4,487,474 A * | 12/1984 | Nishie | ................... | G02B 6/3825 385/66 |
| 4,615,581 A * | 10/1986 | Morimoto | ........... | G02B 6/3822 385/60 |
| 4,676,588 A * | 6/1987 | Bowen | ................... | G02B 6/382 385/62 |
| 4,690,494 A * | 9/1987 | Hirose | ................. | G02B 6/3807 385/60 |
| 4,752,111 A * | 6/1988 | Fisher | ................... | G02B 6/3847 385/55 |
| 4,805,980 A * | 2/1989 | Mackenroth | ........... | G02B 6/264 385/60 |
| 4,913,523 A * | 4/1990 | Yoshida | ............... | G02B 6/3874 385/15 |
| 5,078,467 A * | 1/1992 | Blomgren | ............ | G02B 6/3806 385/55 |
| 5,237,984 A * | 8/1993 | Williams, III | ..... | A61B 1/00142 359/510 |
| 5,423,312 A * | 6/1995 | Siegmund | .............. | A61B 1/042 385/133 |
| 6,065,882 A * | 5/2000 | Roller | ................... | G02B 6/3814 385/136 |
| 6,139,194 A * | 10/2000 | Bella | ...................... | G02B 6/382 362/551 |
| 6,195,477 B1 * | 2/2001 | Denuto | ................ | G02B 6/3878 362/551 |
| 6,203,208 B1 * | 3/2001 | Stupar | ................. | G02B 6/3809 362/581 |
| 6,450,677 B1 * | 9/2002 | Knauer | .................... | B60Q 7/00 362/511 |
| 7,182,522 B2 * | 2/2007 | Sasaki | .................... | G02B 6/389 385/53 |
| 7,325,977 B2 * | 2/2008 | Stevens | ................ | G02B 6/3851 385/53 |
| 7,356,054 B2 * | 4/2008 | Hama | ................ | A61B 1/00096 372/21 |
| 7,422,356 B2 * | 9/2008 | Hama | ................. | A61B 1/0653 362/129 |
| 7,513,694 B2 * | 4/2009 | Sasaki | .................. | G02B 6/3825 385/60 |
| 7,758,224 B2 * | 7/2010 | Hama | ................. | A61B 1/0653 362/231 |
| 8,197,111 B2 * | 6/2012 | Hama | ................. | A61B 1/0653 362/231 |
| 9,228,725 B2 * | 1/2016 | Ito | ............................ | A61B 1/07 |
| 2003/0012533 A1 * | 1/2003 | Steiner | .................. | G01N 21/05 385/121 |
| 2004/0064019 A1 * | 4/2004 | Chang | ................ | A61B 1/00059 600/180 |
| 2004/0101265 A1 * | 5/2004 | Jong | .................... | G02B 6/3807 385/134 |
| 2005/0191009 A1 * | 9/2005 | Kraas | .................... | G02B 6/403 385/53 |
| 2005/0220420 A1 * | 10/2005 | Sasaki | .................... | G02B 6/389 385/55 |
| 2006/0013537 A1 * | 1/2006 | Miyake | ................ | G02B 6/3833 385/60 |
| 2006/0051028 A1 * | 3/2006 | Sasaki | .................. | G02B 6/3825 385/55 |
| 2006/0257079 A1 | 11/2006 | Ohtsuka et al. | | |
| 2009/0040781 A1 * | 2/2009 | Ito | ........................ | A61B 1/0653 362/554 |
| 2010/0069747 A1 * | 3/2010 | Watanabe | ............ | A61B 5/0066 600/427 |
| 2010/0247040 A1 * | 9/2010 | Kuriki | .................. | G02B 6/3821 385/72 |
| 2011/0141763 A1 * | 6/2011 | Kamee | .................. | G02B 6/0008 362/583 |
| 2012/0178992 A1 * | 7/2012 | Fujimoto | ........... | A61B 1/00006 600/109 |
| 2012/0307515 A1 * | 12/2012 | Fukui | ................. | C09K 11/7706 362/556 |
| 2013/0183006 A1 * | 7/2013 | Yu | ............................ | G02B 6/36 385/78 |
| 2014/0022810 A1 * | 1/2014 | Ito | ........................... | A61B 1/07 362/551 |
| 2014/0055562 A1 * | 2/2014 | Demers | ................ | H04N 5/2256 348/45 |
| 2014/0146559 A1 * | 5/2014 | Ito | ........................... | A61B 1/05 362/583 |

FOREIGN PATENT DOCUMENTS

| | | |
|---|---|---|
| JP | 08-254658 A | 10/1996 |
| JP | 10-137184 A | 5/1998 |
| JP | 2001-215362 A | 8/2001 |
| JP | 2003-225196 A | 8/2003 |
| JP | 2005-205195 A | 8/2005 |
| JP | 2006-317890 A | 11/2006 |
| JP | 2013-33158 A | 2/2013 |
| WO | 2011/004801 A1 | 1/2011 |

OTHER PUBLICATIONS

Extended Supplementary European Search Report dated Dec. 11, 2014 from related European Application No. 12 82 0296.7.

International Search Report dated Oct. 23, 2012 issued in PCT/JP2012/069480.

European Patent Office Communication dated Jun. 29, 2016 in corresponding European Application No. 12 820 296.7.

* cited by examiner

LIGHT SOURCE APPARATUS

CROSS-REFERENCE TO RELATED APPLICATIONS

This application is a Continuation application of PCT Application No. PCT/JP2012/069480, filed Jul. 31, 2012 and based upon and claiming the benefit of priority from the prior Japanese Patent Application No. 2011-169506, filed Aug. 2, 2011, the entire contents of which are incorporated herein by reference.

BACKGROUND OF THE INVENTION

1. Field of the Invention

The present invention relates to a light source apparatus that enables light emitted from a light source to be led with the use of a light guide path.

2. Description of the Related Art

For example, Jpn. Pat. Appln. KOKAI Publication No. 2005-205195 discloses a prior art of a light source apparatus that emits illumination light. In the Publication, a light emission apparatus having a light emission unit is suggested, the light emission unit including a laser beam source, a light guide formed out of an optical fiber, and a wavelength conversion member. Herein, a blue laser beam source is arranged at a proximal end portion of the light guide formed out of the optical fiber and the wavelength conversion member is arranged at a distal end portion of the light guide, respectively. Further, in this constitution, a laser beam (primary light) emitted from the blue laser beam source is led to a distal end through the light guide, and secondary light subjected to wavelength conversion by the wavelength conversion member at the distal end of the light guide is allowed to exit to the outside as illumination light.

This light source apparatus is mounted in, e.g., an endoscope. According to this endoscope, a light emission unit (a wavelength conversion member) is to be inserted into a narrow space to illuminate the inside of the narrow space.

In Jpn. Pat. Appln. KOKAI Publication No. 2005-205195, the light source apparatus is mounted in, e.g., an endoscope, the light emission unit (the wavelength conversion member) is inserted into a narrow space with use of the endoscope, and the inside of the narrow space is illuminated. In this case, at the time of an operation of inserting the endoscope into the narrow space, a shape of the endoscope changes in accordance with a shape of the inside of the space into which the endoscope is inserted, and hence a shape of the light guide must be changed in accordance with the shape of the endoscope at this moment. When the change of shape or the like of the light guide is repeatedly carried out in this manner, the optical fiber may possibly be damaged. When the optical fiber is damaged, the laser beam emitted from the laser beam source does not reach the wavelength conversion member provided at the distal end portion of the light guide, and the light source apparatus cannot emit the light.

Furthermore, in the case of repairing the light source apparatus according to Jpn. Pat. Appln. KOKAI Publication No. 2005-205195, one end side of the damaged optical fiber must be removed from the laser beam source, and the other end side of the same must be removed from the wavelength conversion member. Moreover, after this operation, one end side of a new optical fiber must be disposed to the laser beam source, and the other end side of the new optical fiber must be disposed to the wavelength conversion member. Therefore, the repair takes large amounts of time and effort at the time of replacing the optical fiber.

In a light source apparatus with a narrow diameter that illuminates a narrow tube in particular, a diameter of a wavelength conversion member must be narrowed. In this case, reuse of the wavelength conversion member is difficult, the wavelength conversion member must be replaced with a new one, and a cost is increased.

Additionally, when the wavelength conversion member is deteriorated or when the laser beam source apparatus is deteriorated, likewise, there occurs a problem that an optical fiber must be attached or removed. That is, the light source apparatus according to the conventional technology has a configuration that causes inconvenience during repair.

BRIEF SUMMARY OF THE INVENTION

In view of the above-described problems, it is an object of the present invention to provide a light source apparatus that can be safely and easily repaired even if a failure occurred in part of the apparatus.

According to an aspect of the invention, there is provided a light source apparatus comprising:

a primary light source module including a primary light source configured to emit primary light;

a light conversion module including a light conversion unit configured to convert optical properties of the primary light emitted from the primary light source and to generate secondary light;

a light guide path, arranged between the primary light source module and the light conversion module, configured to guide the primary light emitted from the primary light source to the light conversion module from the primary light source module;

a first connecting portion configured to connect detachably the light conversion module with the light guide path; and a second connecting portion configured to connect detachably the primary light source module with the light guide path.

According to the present invention, it is possible to provide a light source apparatus that can be safely and easily repaired even if a failure occurred in part of the apparatus.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Embodiments according to the present invention will now be described hereinafter with reference to the drawings.

First Embodiment

Figure 1:
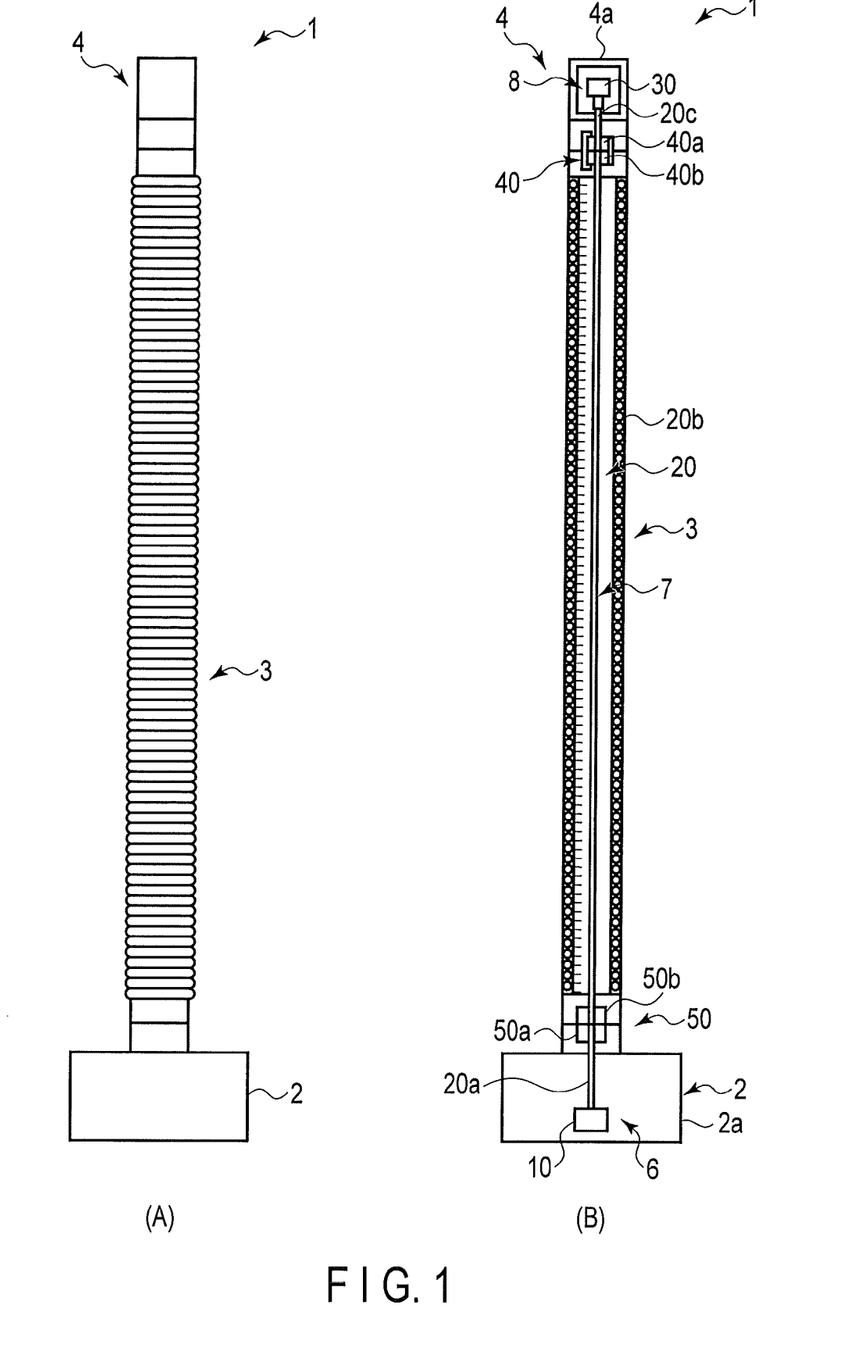
FIG. 1(A) is a side view showing an appearance of an entire illumination apparatus according to a first embodiment of the present invention.
FIG. 1(B) is a longitudinal sectional view showing an internal configuration of the illumination apparatus.
Figure 2:
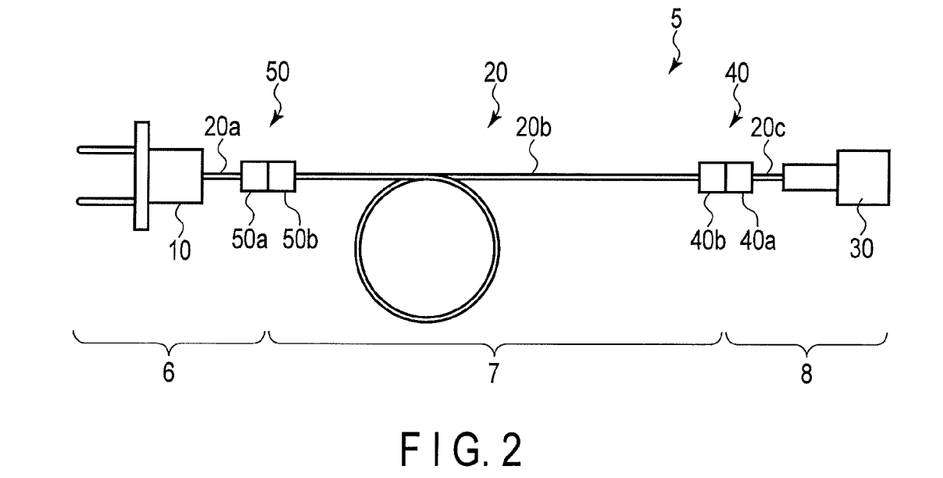
FIG. 2 is a side elevation showing an outline configuration of an entire light source apparatus incorporated in the illumination apparatus according to the first embodiment.

FIG. 1(A), FIG. 1(B), FIG. 2, FIG. 3(A) and FIG. 3(B) show a first embodiment according to the present invention. This embodiment is an example where a light source apparatus 5 according to the present invention shown in FIG. 2 is incorporated in an illumination apparatus 1 such as an illumination stand depicted in FIG. 1(A). In this illumination apparatus 1, a flexibly-deformable shaft body 3 is erected on a base 2. An illumination light exit portion 4 is arranged at an upper end portion of the shaft body 3.

The shaft body 3 is formed out of, e.g., a flexible pipe. When this flexible pipe is expanded or contracted to bend the shaft body 3, the illumination light exit portion 4 can be set to face an arbitrary direction.

FIG. 2 shows an outline configuration of a light source apparatus 5 according to this embodiment. The light source apparatus 5 according to this embodiment includes a primary light source 10, a light guide path 20, and a conversion unit 30, as a basic configuration. The primary light source 10 emits primary light. The light conversion unit 30 converts optical properties of the primary light and allows the converted light to exit therefrom as secondary light. Here, the light conversion unit 30 converts at least one of a peak waveform, a spectral shape, and a radiation angle of the primary light and allows the converted light to exit therefrom as secondary light. The light guide path 20 is formed out of an elongated optical fiber along which the primary light exiting from the primary light source 10 is guided to the light conversion unit 30.

The primary light source 10 is incorporated in a later-described primary light source module 6. The light conversion unit 30 is incorporated in a later-described light conversion module 8. A later-described optical fiber module 7 is arranged between the primary light source module 6 and the light conversion module 8.

Two connecting portions (a first connecting portion 40 and a second connecting portion 50) are provided to the light guide portion 20. The first connecting portion 40 detachably connects the light guide portion 20 with the light conversion unit 30, and the second connecting portion 50 detachably connects the primary light source 10 with the light guide portion 20. Here, a light conversion unit side connector 40a and a light guide portion side connector 40b are provided in the first connecting portion 40. Further, the light conversion unit side connector 40a and the light guide portion side connector 40b are detachably connected to each other. Likewise, a primary light source side connector 50a and a light guide portion side connector 50b are provided in the second connecting portion 50. Furthermore, the primary light source side connector 50a and the light guide portion side connector 50b are detachably connected to each other.

Moreover, the primary light source module 6 includes a first optical fiber 20a connected to the primary light source 10, the light guide path 20 includes a second optical fiber 20b, and the light conversion module 8 includes a third optical fiber 20c connected to the light conversion unit 30.

A configuration of each portion will now be described hereinafter in more detail.

[Primary light Source Module]

The primary light source module 6 is constituted of the primary light source 10, the first optical fiber 20a, and the primary light source side connector 50a of the second connecting portion 50. As the primary light source 10, for example, a semiconductor laser can be used. In this embodiment, the primary light source 10 is formed out of, e.g., a blue semiconductor laser having a wavelength of 450 nm. When the semiconductor laser is used, the primary light can be efficiently allowed to enter the first optical fiber 20a.

The primary light source 10 is connected to one end of the first optical fiber 20a. The primary light source side connector 50a of the second connecting portion 50 is connected to the other end of the first optical fiber 20a. The primary light source module 6 is fixed to a housing or the like of the base 2 of the illumination apparatus 1. Here, in the housing of the base 2 in the illumination apparatus 1, the primary light source side connector 50a is fixed to an upper end central region of a base main body 2a formed out of a light shielding member that blocks transmission of a laser beam. That is, the primary light source 10, the first optical fiber 20a, and the primary light source side connector 50a are fixed to the base main body 2a which is a common housing of the base 2. As a result, the first optical fiber 20a is prevented from bending when the light source apparatus 5 is used.

[Light Conversion Module]

The light conversion module 8 is constituted of the light conversion unit 30, the third optical fiber 20c, and the light conversion unit side connector 40a of the first connection unit 40. The light conversion unit 30 has a function of converting optical properties of the primary light, e.g., at least one of a peak wavelength, a spectral shape, and a radiation angle of the primary light. For example, as the light conversion unit 30, it is possible to use a light diffusion unit that expands a radiation angle of the primary light, a phosphor unit that converts all of a peak wavelength, a spectral shape, and a radiation angle, or the like.

The light conversion unit 30 is connected to one end of the third optical fiber 20c. The light conversion unit side connector 40a is provided at the other end of the third optical fiber 20c. Further, the light conversion module 8 is fixed to a common housing of the illumination exit portion 4 in the illumination apparatus 1. Here, in the illumination light exit portion 4, the light conversion unit side connector 40a is fixed to a lower end central region of an illumination light exit portion cover 4a that allows illumination light to transmit therethrough. That is, the light conversion unit 30, the third optical fiber 20c, and the light conversion unit side connector 40a of the first connecting portion 40 are fixed to the illumination light exit portion cover 4a which is a common housing of the illumination light exit portion 4. As a result, the third optical fiber 20c is prevented from bending when the light source apparatus 5 is used.

[Optical Fiber Module]

The optical fiber module 7 is constituted of the elongated second optical fiber 20b having flexibility, the light guide portion side connector 50b fixed to one end of this second optical fiber 20b, and the light guide portion side connector 40b fixed to the other end of the second optical fiber 20b. This optical fiber module 7 is incorporated in the shaft body 3 of the illumination apparatus 1. Here, the light guide portion side connector 50b is fixed to a lower end portion of the shaft body 3, and the light guide portion side connector 40b is fixed to an upper end portion of the same. Furthermore, the second optical fiber 20b can bend together with the shaft body 3 when the light source apparatus 5 is used and the shaft body 3 of the illumination apparatus 1 is operated to bend in an arbitrary direction by an operation from the outside. As a result, the light conversion unit 30 which is a distal end portion of the light source apparatus 5 can be set to face a direction to be illuminated by an external operation.

[Light Source Apparatus]

The light source apparatus 5 is formed out of a combination of the primary light source module 6, the optical fiber module 7, and the light conversion module 8. In this embodiment, as the primary light source 10, for example, a blue semiconductor laser having a wavelength of 450 nm is used. As each of the optical fibers 20a, 20b, and 20c, a glass step-index type optical fiber having a core diameter of 50 µm, a clad diameter of 125 µm, and NA=0.22 is used. The light conversion unit 30 is configured to allow bright white light to efficiently exit therefrom by using a phosphor such as YAG;Ce that absorbs blue light and emits yellow light.

[Connecting Portion]

The light source apparatus 5 according to this embodiment has two connecting portions (the first connecting portion 40 and the second connecting portion 50). The light conversion unit side connector 40a and the light guide portion side connector 40b are detachably coupled with each other as the first connecting portion 40 between the second optical fiber 20b and the third optical fiber 20c. The primary light source side connector 50a and the light guide portion side connector 50b are detachably coupled with each other as the second connecting portion 50 between the first optical fiber 20a and the second optical fiber 20b.

Here, the second connecting portion 50 provided between the primary light source module 6 and the optical fiber module 7 is a connecting portion that can be used for a purpose other than repair. That is, the second connecting portion 50 is a connecting portion that can be used by an end user. For example, to obtain illumination light that meets a purpose, the second connecting portion 50 can be used for replacing and connecting the arbitrary primary light source module 6 and the arbitrary light conversion module 8. Therefore, a safety measure such as a non-illustrated shutter or a primary light source interlock system is taken for the second connecting portion 50 so that the primary light does not leak to the outside even if the primary light source side connector 50a and the light guide portion side connector 50b are decoupled. That is, the second connecting portion 50 is configured to improve a safety level as compared with the first connecting portion 40.

On the other hand, the first connecting portion 40 between the light conversion module 8 and the optical fiber module 7 is a connecting portion that is exclusively used for repair, maintenance, and manufacture of the light source apparatus 5. That is, an end user does not attach or detach the first connecting portion 40, and this connecting portion is a connecting portion that is attached or detached when a person having knowledge or a skill for assuring safety of the primary light, e.g., a person who is in charge of manufacture or repair uses a comparable environment or facilities. Therefore, differing from the second connecting portion 50, a safety measure is not taken for the first connecting portion 40 itself. Further, since the first connecting portion 40 is provided on the distal end side of the optical fiber module 7, it is inserted into an observation target, e.g., a tube. Therefore, the first connecting portion 40 must be fabricated into a narrow and small shape. Thus, an area of a section of the first connecting portion 40 taken along a plane orthogonal to a light guiding direction of the primary light is smaller than that of the second connecting portion 50.

Access restriction is applied to the first connecting portion 40 so that the first connecting portion 40 cannot be accidentally removed by a user. An example of the access restriction is that the first connecting portion 40 cannot be removed unless a tool 64 is used. In other words, in the first connecting portion 40, an access restricting portion 61 is formed, the access restricting portion 61 being subjected to tool type access restriction so that it cannot be easily removed by an operation of a user during use of the light source apparatus 5.

Figure 3:
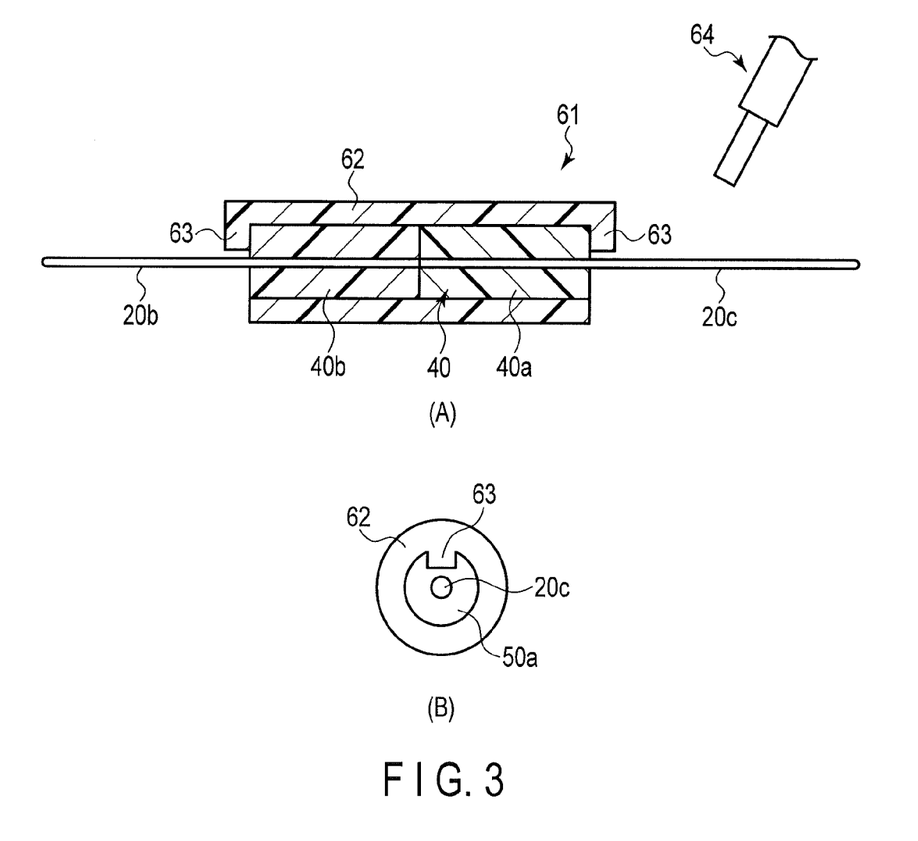
FIG. 3(A) is a longitudinal sectional view of a primary part showing a coupling portion of a first connecting portion that detachably connects a ferrule fixed to a connection end of an optical fiber of a light guide path in the light source apparatus according to an embodiment with a ferrule fixed to a connection end of a light guide optical fiber in a light conversion unit.
FIG. 3(B) is a side elevation showing an end face of the coupling portion of the first connecting portion in FIG. 3(A)

FIG. 3(A) is a cross-sectional view showing an example of the access restricting portion 61 of the first connecting portion 40. As shown in FIG. 3(A), the light conversion unit side connector 40a and the light guide portion side connector 40b of the first connecting portion 40 are formed as, e.g., ferrules or the like, and the first connecting portion 40 is a small connector that inserts such connectors 40a and 40b into a cylindrical sleeve 62 and connects them.

Furthermore, fixing engagement protrusions 63 are provided at both ends of the sleeve 62 formed by bending and deforming each of both the ends of the sleeve 62 at a substantially right angle toward the central direction as shown in FIG. 3(B), the fixing engagement protrusions 63 locking the light conversion unit side connector 40a and the light guide portion side connector 40b of the second connecting portion 50 in a coupled state. These engagement protrusions 63 hold the connectors 40a and 40b so that the light conversion unit side connector 40a and the light guide portion side connector 40b of the first connecting portion 40 cannot be easily removed from the sleeve 62. Moreover, the ferrule of the light conversion unit side connector 40a or the light guide portion side connector 40b of the first connecting portion 40 can be removed from the sleeve 62 by an access restriction canceling operation for deforming each engagement protrusion 63 with the use of a tool 64 or the like as required. As a result, the access restriction of the access restricting portion 61 is canceled by the predetermined access restriction canceling operation to enable an attaching or detaching operation between the light conversion unit side connector 40a and the light guide portion side connector 40b of the first connecting portion 40.

On the other hand, the second connecting portion 50 is configured with higher resistance against repetition of attachment/detachment as compared with the first connecting portion 40, and it is configured with high abrasion resistance in a contact region that is brought into contact and slid at the time of the attaching/detaching operation.

A function of the thus configured light source apparatus 5 will now be described. A basic operation of the light source apparatus 5 according to this embodiment will be first explained. In the case of using the light source apparatus 5, a user supplies electric power to the primary light source 10 from a non-illustrated power supply to emit the primary light. The primary light emitted from the primary light source 10 enters the first optical fiber 20a and is led to the primary light source side connector 50a of the second connecting portion 50. In the second connecting portion 50, the first optical fiber 20a of the primary light source side connector 50a is optically connected to the second optical fiber 20b of the light guide portion side connector 50b, and the primary light led through the first optical fiber 20a is allowed to enter the second optical fiber 20b.

The primary light that entered the second optical fiber 20b is led to the first connecting portion 40 through the second optical fiber 20b. In the first connecting portion 40, the second optical fiber 20b of the light guide portion side connector 40b is optically connected to the third optical fiber 20c of the light conversion unit side connector 40a, and the primary light guided through the second optical fiber 20b is allowed to enter the third optical fiber 20c. The primary light that entered the third optical fiber 20c is guided to the light conversion unit 30 through the third optical fiber 20c. The light conversion unit 30 converts the guided primary light and discharges it to the outside as illumination light that is secondary light.

In the case of installing the light source apparatus 5 according to the present invention into the illumination apparatus 1 such as an illumination stand shown in FIG. 1(A) and using it in this state, the illumination light exit portion 4 is set to face a desired direction and illumination is carried out by expanding or contracting a flexible pipe of the shaft body 3 to bend the shaft body 3. At this time, when the shaft body 3 of the illumination apparatus 1 is operated to bend in an arbitrary direction by an operation from the outside, the second optical fiber 20b bends together with the shaft body 3.

Therefore, of the three optical fibers (the first optical fiber 20a, the second optical fiber 20b, and the third optical fiber 20c) of the light source apparatus 5, the second optical fiber 20b is the most frequently bent optical fiber. Therefore, damage to the optical fiber due to repeated bending highly possibly occurs in the second optical fiber 20b. For example, when the second optical fiber 20b is damaged, a user asks, e.g., a person in charge of repair for repair in a state that the second connecting portion 50 between the primary light source module 6 and the optical fiber module 7 is removed and the optical fiber module 7 is connected to the light conversion module 8.

The person who is in charge of repair and accepted the repair request performs the access restriction canceling operation in which an operator having an appropriate skill deforms each engagement protrusion 63 of the access restricting portion 61 of the first connecting portion 40 with the use of the tool 64 or the like suitable for the access restriction canceling operation in an environment that is adequate for the repair operation. Based on this access restriction canceling operation, the ferrule of the light conversion unit side connector 40a of the first connecting portion 40 and the ferrule of the light guide portion side connector 40b can be removed from the sleeve 62. As a result, the optical fiber module 7 and the light conversion module 8 are disconnected in the first connecting portion 40.

Additionally, after disconnecting the optical fiber module 7 and the light conversion module 8, the operator connects a new optical fiber module 7 with the first connecting portion 40 and completes the repair.

Further, when the light conversion module 8 fails to operate properly, likewise, a user asks a person in charge of repair or the like for the repair in a state that the second connecting portion 50 between the primary light source module 6 and the optical fiber module 7 is removed and the optical fiber module 7 is connected to the light conversion module 8. Therefore, as described above, the operator in charge of repair deforms each engagement protrusion 63 of the access restricting portion 61 in the first connecting portion 40 with the use of, e.g., the tool 64 and thereby removes the ferrule of the light conversion unit side connector 40a of the first connecting portion 40 and the ferrule of the light guide portion side connector 40b from the sleeve 62. As a result, the optical fiber module 7 and the light conversion module 8 are disconnected in the first connecting portion 40, and the new light conversion module 8 is connected to the first connecting portion 40, and the repair is completed.

Furthermore, when the primary light source module 6 fails to operate properly, the user removes the primary light source module 6 at the second connecting portion 50 and asks a person in charge of repair or the like for repair of the primary light source module 6. The person in charge of repair determines a state of the primary light source module 6 and repairs or replaces the primary light source module 6.

When the above-described configuration is adopted, a faulty part of the optical fiber module 7 alone can be easily removed and subjected to replacement or repair. Moreover, a position of the first connecting portion 40 can be appropriately selected so that a portion of the optical fiber module 7 that may highly possibly fail to operate properly can be easily replaced.

Thus, the light source apparatus 5 having the above-described configuration exercises the following effect. That is, in the light source apparatus 5 according to this embodiment, the two connecting portions (the first connecting portion 40 and the second connecting portion 50) are provided on the light guide portion 20. As a result, if a failure occurs in the light source apparatus 5, the first connecting portion 40 and the second connecting portion 50 can be removed, a portion where the failure occurred (e.g., the faulty second optical fiber 20b in the optical fiber module 7)

can be removed, and this portion alone can be replaced. As a result, the repair can be easily carried out. Moreover, since only the second optical fiber 20b in the optical fiber module 7 that is apt to fail to operate the most can be replaced, expensive components, e.g., the light conversion unit 30 in the light conversion module 8 or the primary light source 10 in the primary light source module 6 can be reused without replacing. Therefore, a member cost at the time of repairing the light source apparatus 5 can be reduced.

It is to be noted that since the first optical fiber 20a of the primary light source module 6 and the third optical fiber 20c of the light conversion module 8 are configured not to bend when the light source apparatus 5 is used, a possibility of damage to the first optical fiber 20a or the third optical fiber 20c is low. Additionally, since the first optical fiber 20a of the primary light source module 6 and the third optical fiber 20c of the light conversion module 8 are configured in such a manner that these optical fibers are arranged in the housing without being exposed to the outside by shortening their lengths, the optical fibers 20a and 20c are not exposed to the outside of the modules. As a result, the possibility of damage to the first optical fiber 20a of the primary light source module 6 and the third optical fiber 20c of the light conversion module 8 can be reduced at the time of manufacture or repair.

Therefore, according to the configuration of this embodiment, even if the light source apparatus 5 fails to operate properly, it can be easily repaired or replaced.

Further, in this embodiment, the first connecting portion 40 that enables attachment or detachment of the light guide portion 20 and the light conversion unit 30 has the access restricting portion 61 that prohibits the attaching/detaching operation relative to the light guide portion 20 and the light conversion unit 30, and it cancels the access restriction of the access restricting portion 61 by the predetermined access restriction canceling operation and enables attachment/detachment between the light guide portion 20 and the light conversion unit 30. Therefore, since it is possible to prevent the last user from attaching or detaching the first connecting portion 40, the light source apparatus 5 can be repaired in the correct order so that a person having knowledge or a skill for securing safety of the primary light, e.g., a person in charge of manufacture or repair can perform the operation of attaching or detaching the first connecting portion 40 with the use of an appropriate environment or facilities.

As described above, according to this embodiment, the light source apparatus 5 that can be easily repaired can be provided.

It is to be noted that a user can use the second connecting portion 50 whereas the user cannot use the first connecting potion 40 in this embodiment, but the present invention is not restricted thereto. For example, both the first and second connecting portions 40 and 50 may not be used by the user. When such a configuration is adopted, safety and other measures do not have to be taken for both the first and second connecting portions 40 and 50, and an inexpensive light source apparatus 5 can be provided. Furthermore, both the first and second connecting portions 40 and 50 can be used by the user. When such a configuration is adopted, the user need only hand over the minimum number of components to a person in charge of manufacture or repair at the time of repair. Moreover, the replacement alone can be carried out by the user.

Second Embodiment

Figure 4:
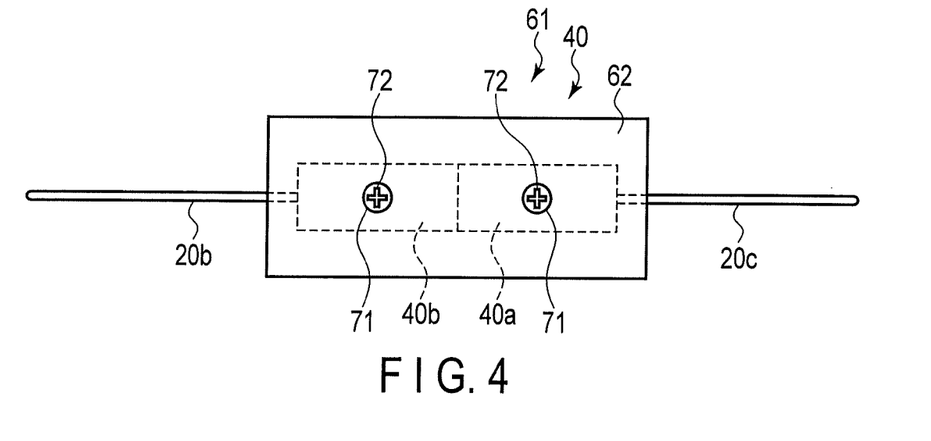
FIG. 4 is a side elevation showing a second embodiment according to the present invention.

FIG. 4 shows a second embodiment. This embodiment is a first modification of the access restricting portion 61 in the first connecting portion 40 in the light source apparatus 5 according to the first embodiment. An access restricting portion 61 in a first connecting portion 40 according to this modification includes a cylindrical sleeve 62 and male screws 71 provided in joint portions of a light conversion unit side connector 40a and a light guide portion side connector 40b. A cross-shaped engagement groove 72 that engages with a non-illustrated cross-shaped driver is provided on a head portion of this male screw 71.

Additionally, an access restriction canceling operation of engaging the non-illustrated cross-shaped driver with the cross-shaped engagement grooves 72 and removing the male screws 71 enables removing ferrules of the light conversion unit side connector 40a and the light guide portion side connector 40b in the first connecting portion 40 from the sleeve 62. Such a predetermined access restriction canceling operation enables canceling the access restriction of the access restricting portion 61 and effecting an attaching/detaching operation for the light conversion unit side connector 40a and the light guide portion side connector 40b in the first connecting portion 40.

It is to be note that a slotted engagement groove and a slotted driver or the like may be used in place of the cross-shaped engagement groove 72 and the cross-shaped driver.

Third Embodiment

Figure 5:
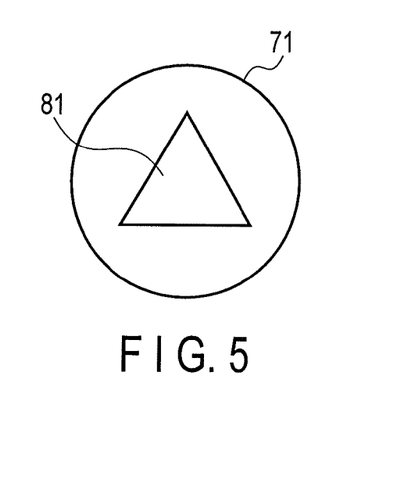
FIG. 5 is a plan view showing an example of a tool of a special screw in a third embodiment according to the present invention.
Figure 6:
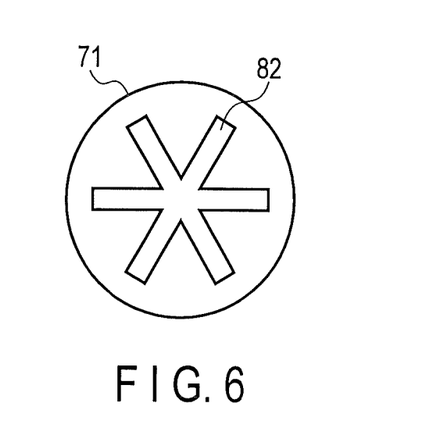
FIG. 6 is a plan view showing another example of the tool of the special screw.

FIG. 5 and FIG. 6 show a third embodiment. This embodiment is a second modification of the access restricting portion 61 in the first connecting portion 40 of the light source apparatus according to the first embodiment. In an access restricting portion 61 of a first connecting portion 40 according to this modification, male screws 71 disposed to a joint portion of a cylindrical sleeve 62 and a light conversion unit side connector 40a and a joint portion of the sleeve 62 and a light guide portion side connector 40b respectively are special screws. That is, there is adopted each special screw having a triangular concave portion 81 formed on a head portion of the male screw 71 as shown in FIG. 5 or each special screw having a groove portion 82 with a special shape such that three linear grooves cross over each other as shown in FIG. 6. In this case, it is desirable to combine a specially-shaped tool having an engagement convex portion associated with the triangular concave portion 81 shown in FIG. 5 or the specially-shaped groove portion 82 shown in FIG. 6. It is to be noted that, conversely, a triangular convex portion shown in FIG. 5 or a specially-shaped convex portion shown in FIG. 6 may be provided on the head portion of the male screw 71, and a concave portion associated with such a portion may be provided on a specially-shaped tool. That is, it is desirable for the access restricting portion 61 to correspond to a tool type access restriction having a distal end configuration of the special tool and a fitting configuration of the special screw having a special shape associated with this tool.

Furthermore, as another example, each screw to be used may be a backward screw that can be removed when rotated in a direction that is opposite to a regular direction. As still another example, a connector that requires two actions, e.g., pushing and turning may be adopted. At this time, when a turning direction of a screw adopted for fixation using the screw after pushing is that of a backward screw whose turning direction is opposite to a regular direction, more assured access restriction can be realized.

Fourth Embodiment

Figure 7:
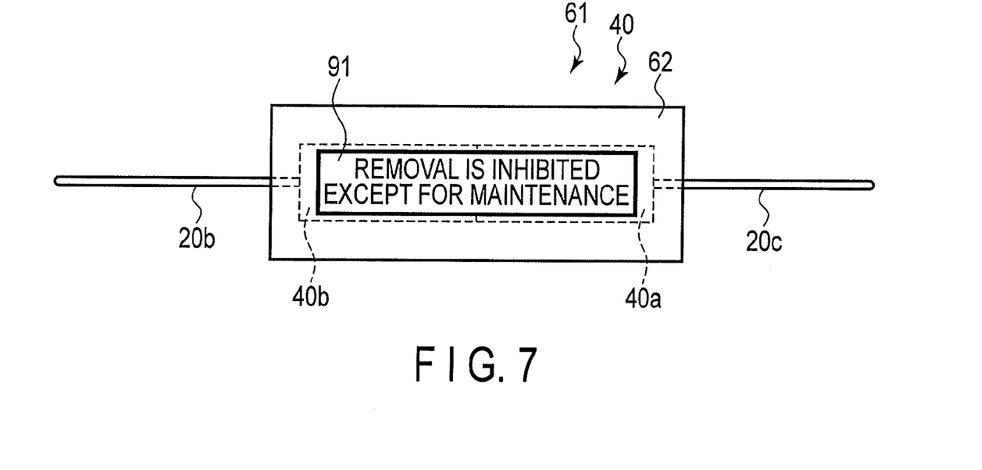
FIG. 7 is a side elevation showing a fourth embodiment according to the present invention.

FIG. 7 shows a fourth embodiment. This embodiment is a third modification of the access restricting portion 61 in the first connecting portion 40 of the light source apparatus 5 according to the first embodiment. In an access restricting portion 61 in a first connecting portion 40 according to this modification, as shown in FIG. 7, a display portion 91 that displays a warning is provided on an outer peripheral surface of the cylindrical sleeve 62 fitted on each of a light conversion unit side connector 40a and a light guide portion side connector 40b. As this warning display, for example, text or symbols such as "REMOVAL IS INHIBITED EXCEPT FOR MAINTENANCE" can be displayed.

As a result, the access restriction for users is effective, and a high level of the access restriction is set so that the first connecting portion 40 cannot be easily removed as compared with a second connecting portion 50.

Fifth Embodiment

Figure 8:
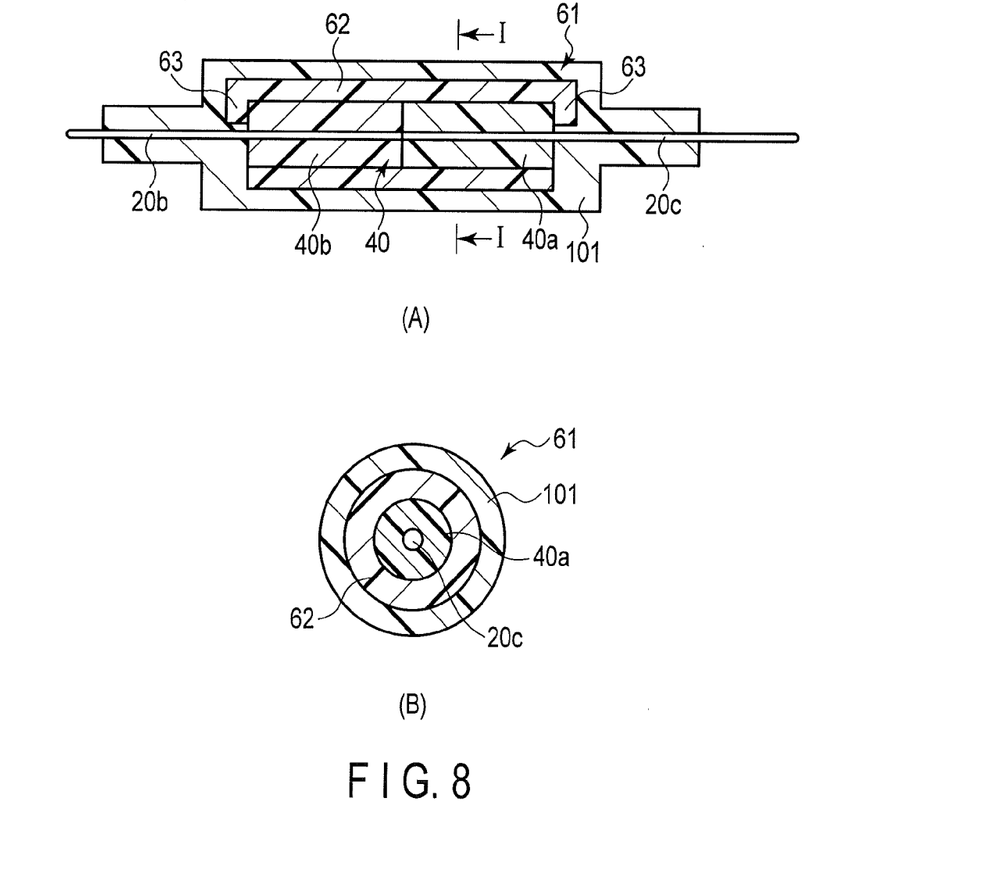
FIG. 8(A) is a longitudinal sectional view of a primary part showing a coupling portion of a first connecting portion in a light source apparatus according to a fifth embodiment of the present invention.
FIG. 8(B) is a sectional view taken along a line I-I in FIG. 8(A)

FIG. 8(A) and FIG. 8(B) show a fifth embodiment. This embodiment is a modification obtained by changing the configuration of the access restricting portion 61 in the first connecting portion 40 of the light source apparatus 5 according to the first embodiment (see FIG. 1(A), FIG. 1(B), FIG. 2, FIG. 3(A), and FIG. 3(B)) as follows. It is to be noted that like reference numerals denote parts equal to those in the first embodiment to omit a description thereof, and different points alone will be described here.

In this modification, as an access restricting portion 61 in a first connecting portion 40 according to the first embodiment, a cover 101 as a protection member that covers a sleeve 62 and an outer peripheral surface of its neighboring region is provided. The cover 101 is made of rubber having waterproof properties, and connection loss of an optical fiber caused when dust or water enters the first connecting portion 40 can be reduced. Further, it is desirable for the cover 101 to have not only waterproof properties but also heat resisting properties, impact resisting properties, and other properties.

Furthermore, in this embodiment, since the first connecting portion 40 is inserted into an illumination target or the like, the first connecting portion 40 is configured with higher waterproof properties, heat resisting properties, or impact resisting properties than those of a second connecting portion 50 so that the illumination target does not have to be selected.

In the case of repairing the light source apparatus 5, an operator having knowledge performs an operation for removing the cover 101 with the use of a necessary tool and then removes the first connecting portion 40 in the same procedure as that in the first embodiment. Moreover, after the repair, a new cover 101 is disposed to the first connecting portion 40.

In the light source apparatus 5 according to this embodiment, since the cover 101 as a protection member that covers the sleeve 62 and an outer peripheral surface of its neighboring region in the access restricting portion 61 of the first connecting portion 40 is provided, a user is prevented from accidentally removing the first connecting portion 40, and the first connecting portion 40 is hard to be removed by a physical impact or the like. Additionally, since the cover 101 prevents dust or water from entering the first connecting portion 40, a reduction in connection loss can be avoided.

Therefore, according to the configuration of this embodiment, since a user does not accidentally remove the first connecting portion 40 for which safety measures are not taken or the first connecting portion 40 is not removed due to a physical impact, a risk of irradiating the user with the primary light can be reduced.

Further, since it is hard for dust or water to enter the first connecting portion 40, a reduction in light volume involved by the connection loss can be avoided. Furthermore, the need for asking an operator for maintenance such as removal of the dust or the water can be reduced.

Furthermore, in this embodiment, since ferrules of a light conversion unit side connector 40a and a light guide portion side connector 40b or the sleeve 62 is not exposed to the outside, members can be selected based on functions without considering environmental properties. For example, it is possible to use, e.g., fragile glass ferrules as required.

Sixth Embodiment

Figure 9:
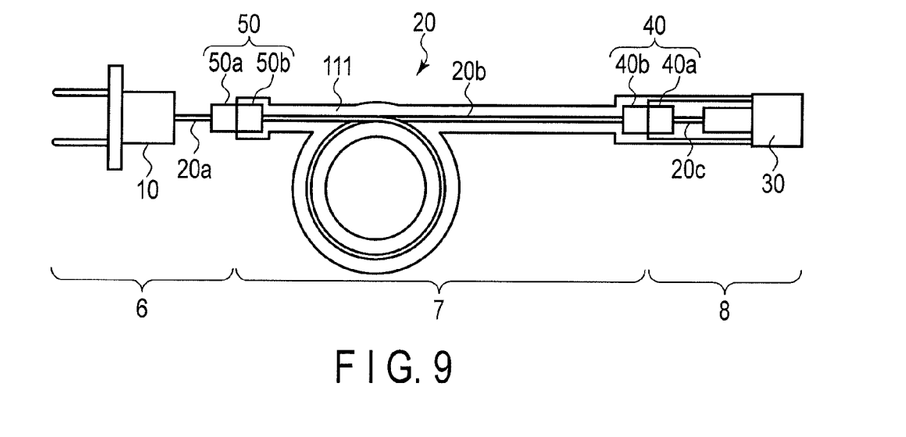
FIG. 9 is a side elevation showing an outline configuration of a light source apparatus according to a sixth embodiment of the present invention.

FIG. 9 shows a sixth embodiment according to the present invention. This embodiment is a modification of the light source apparatus 5 according to the fifth embodiment (see FIG. 8(A) and FIG. 8(B)). Although the fifth embodiment shows the example where the cover 101 is provided around the first connecting portion 40 alone, a cover 111 as a protection member covers the whole from a light conversion module 8 to an optical fiber module 7 in this embodiment. FIG. 9 shows an example where the cover 111 as an access restricting portion is provided in a state that the optical fiber module 7 is connected to the light conversion module 8.

In the light conversion module 8, a light conversion unit 30, a third optical fiber 20c, and a light conversion unit side connector 40a of the first connecting portion 40 are disposed to a common housing of an illumination light exit portion 4 in an illumination apparatus 1. The light conversion module 8 and the optical fiber module 7 are covered with the cover 111 as a common protection member in a state that these modules are connected. The cover 111 may be made of, e.g., rubber having waterproof properties or a heat resisting coat having heat resisting properties. Moreover, it may be made of a cushioning material having excellent impact resisting properties.

When the configuration according to this embodiment is adopted, it is possible to realize a light source apparatus 5 having high resistance properties against a physical impact, an environment, or other factor for the optical fiber module 7 and the light conversion module 8 in addition to the effect of the fifth embodiment.

Seventh Embodiment

Figure 10:
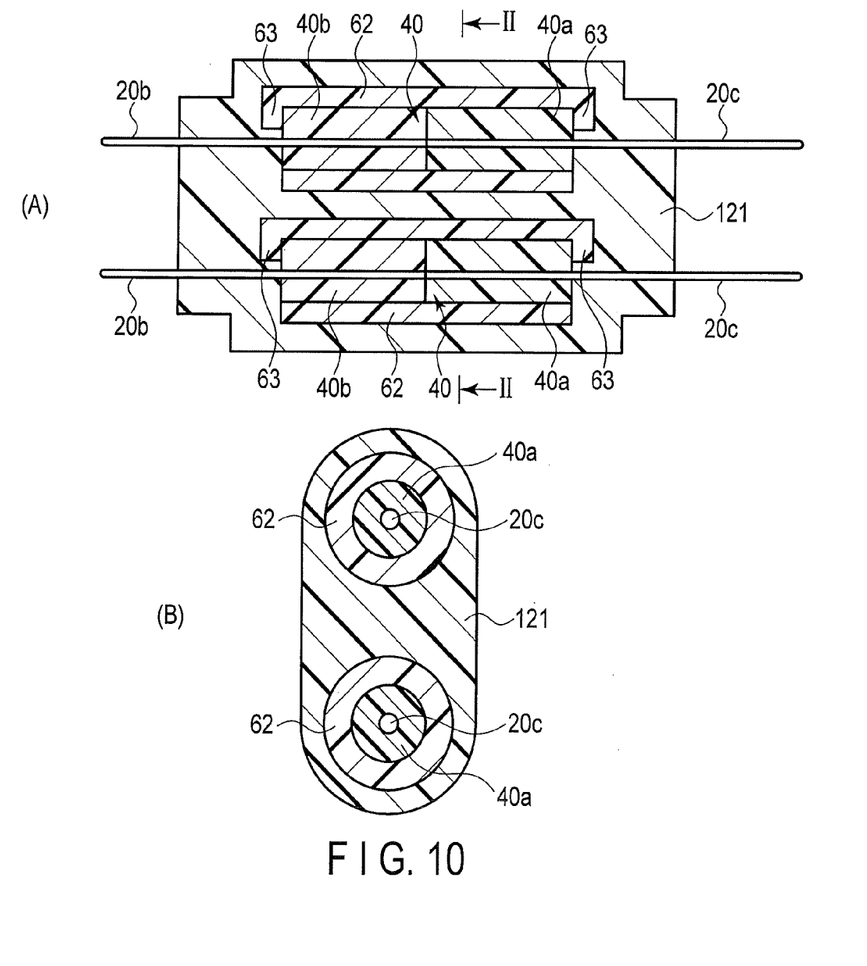
FIG. 10(A) is a longitudinal sectional view of a primary part showing a coupling portion of a first connecting portion in a light source apparatus according to a seventh embodiment of the present invention.
FIG. 10(B) is a sectional view taken along a line II-II in FIG. 10(A)

It is to be noted that the sixth embodiment is the example where the cover 111 as one access restricting portion is provided to one first connecting portion 40, but the present invention is not restricted thereto. For example, like a seventh embodiment shown in FIG. 10(A) and FIG. 10(B), one cover 121 may be provided to two first connecting portions 40. Additionally, it is also preferable to provide one cover with respect to three or more first connecting portions 40. At this time, it is desirable to adopt a configuration where distances between light guide paths in the first connecting portions 40 are small and a degree of integration can be improved.

Further, it is possible to use a so-called multicore connector having a function of connecting light guide paths to one first connecting portion 40. In this case, likewise, it is desirable to adopt a configuration that distances between the light guide paths are small and a degree of integration can be improved.

It is to be noted that the second connecting portion 50 may be also configured with a function of connecting the light guide paths. In this case, since the first connecting portion 40 is inserted into an illumination target or the like, it is desirable to adopt a configuration such that distances between the light guide paths are smaller than those of the second connecting portion 50 and a degree of integration can be improved.

Furthermore, in the foregoing embodiment according to the present invention, the description has been given as to the example where the two connection portions (the first connecting portion 40 and the second connecting portion 50) are provided, but the present invention is not restricted thereto.

When an optical fiber 20b is very long or when more than one bending portion is present, two or more connecting portions can be provided. As a result, a damaged portion of the optical fiber 20b alone can be replaced and repaired.

Eighth Embodiment

Figure 11:
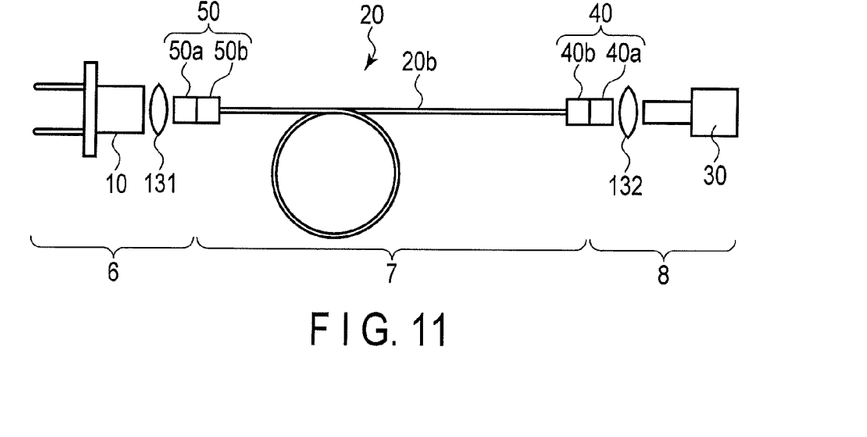
FIG. 11 is a side elevation showing an outline configuration of a light source apparatus according to a eighth embodiment of the present invention.

FIG. 11 shows an eighth embodiment according to the present invention. This embodiment is obtained by changing the configurations of the primary light source module 6 and the light conversion module 8 in the first embodiment. That is, in place of the first optical fiber 20a provided in the primary light source module 6 according to the first embodiment, an optical connecting portion 131 constituted of an optical system such as a lens alone is provided between a primary light source 10 and a primary light source side connector 50a in this embodiment. Likewise, in place of the third optical fiber 20c provided in the light conversion module 8 according to the first embodiment, an optical connecting portion 132 constituted of an optical system such as a lens alone is provided between a light conversion unit 30 and a light conversion unit side connector 40a in this embodiment.

Furthermore, in this embodiment, using the optical connecting portions 131 and 132 in both the primary light source module 6 and the light conversion module 8 enables omitting the use of the optical fibers 20a and 20c in this embodiment.

Ninth Embodiment

Figure 12:
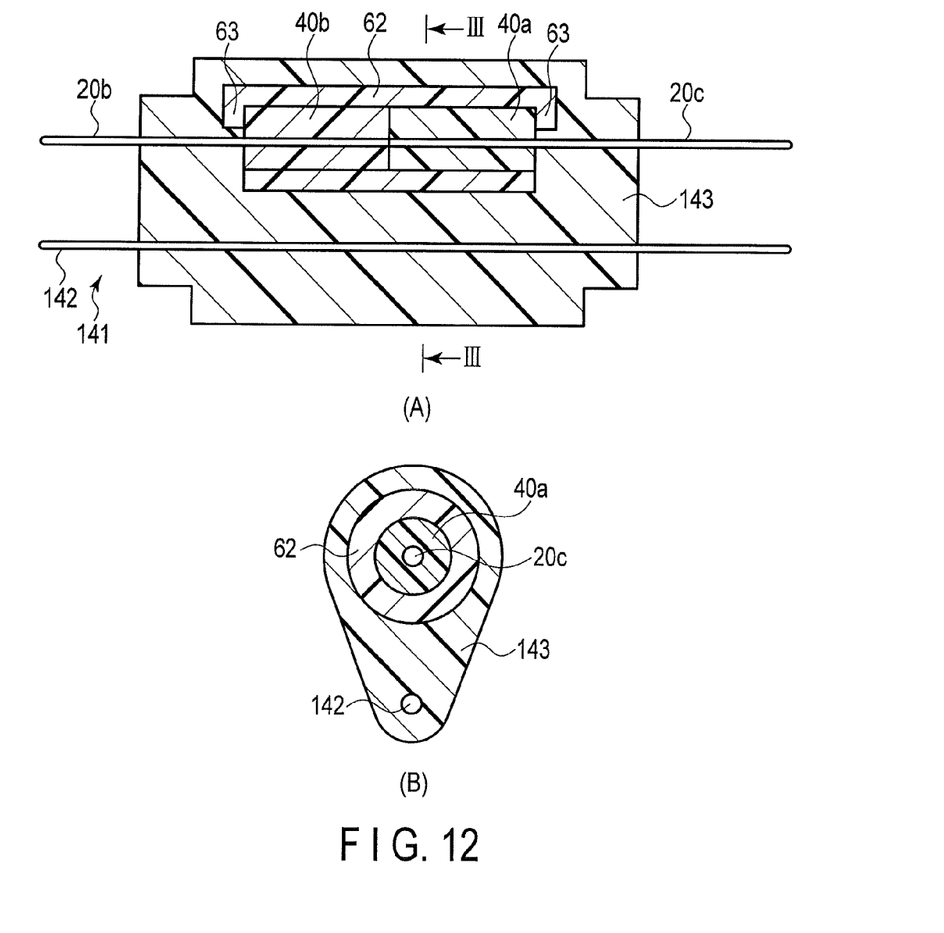
FIG. 12(A) is a longitudinal sectional view of a primary part showing a coupling portion of a first connecting portion in a light source apparatus according to a ninth embodiment of the present invention.
FIG. 12(B) is a sectional view taken along a line III-III in FIG. 12(A)

FIG. 12(A) and FIG. 12(B) show a ninth embodiment according to the present invention. This embodiment is a structural example in which a light source apparatus 5 is used with any other apparatus, e.g., a second apparatus 141 such as an imaging apparatus. FIG. 12(A) shows a peripheral region of a first connecting portion 40 in the light source apparatus 5. Here, for example, an electrical wiring line 142 having no connecting portion alone is arranged in the second apparatus 141, e.g., an imaging apparatus.

Furthermore, the electrical wiring line 142 of the second apparatus 141 is aligned in a peripheral region of the first connecting portion 40 of the light source apparatus 5 in this embodiment, and one cover 143 as a protection member that protects the first connecting portion 40 of the light source apparatus 5 and the electrical wiring line 142 of the second apparatus 141 together is provided.

In this embodiment, since the light source apparatus 5 and the second apparatus 141 that is also used can be protected together by the one cover 143, environmental performance and other aspects of both the light source apparatus 5 and the second apparatus 141 that is also used can be improved.

10th Embodiment

Figure 13:
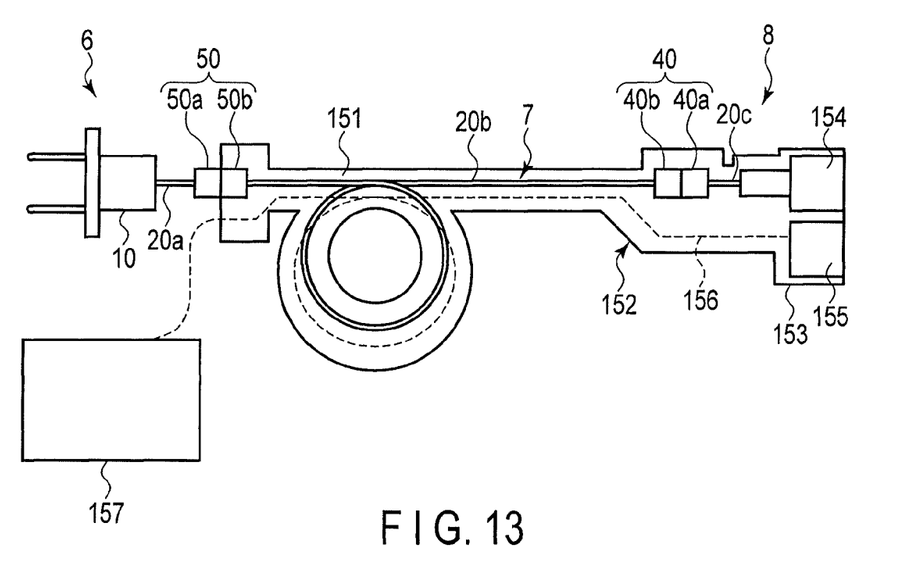
FIG. 13 is a side elevation showing an outline configuration of a light source apparatus according to a tenth embodiment of the present invention.

FIG. 13 shows a 10th embodiment according to the present invention. This embodiment is a structural example when a light source apparatus 5 is used in combination with a second apparatus 152 such as an endoscope having an elongated inserting portion 151 that is inserted into, e.g., a tube.

In the second apparatus 152, a distal end hard portion 153 which is hard is provided at a distal end portion of the inserting portion 151. An illuminating portion 154 as a light conversion unit 30 and an observing portion 155 are provided to this distal end hard portion 153. An imaging element such as a CCD is arranged in the observing portion 155. An electrical wiring line 156 of the imaging element of this observing portion 155 is connected to an external camera control unit (CCU) 157 connected with a proximal end portion of the inserting portion 151 through the inside of the inserting portion 151.

Moreover, in the light source apparatus 5, a light conversion module 8 is installed to the distal end hard portion 153, and an optical fiber module 7 is installed to the inserting portion 151 of the second apparatus 152.

In this embodiment, since the light conversion module 8 and the optical fiber module 7 of the light source apparatus 5 are integrally installed to the inserting portion 151 of the second apparatus 152, there are merits of, e.g., facilitating an inserting operation of inserting the inserting portion 151 into a tube or facilitating standardization of environmental performance.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:
1. A light source apparatus comprising:
a primary light source module including a primary light source configured to emit primary light;
a light conversion module including a light conversion unit configured to convert optical properties of the primary light emitted from the primary light source and to generate secondary light;
a light guide path, arranged between the primary light source module and the light conversion module, configured to guide the primary light emitted from the primary light source to the light conversion module from the primary light source module;
a first connector configured to connect detachably the light conversion module with the light guide path; and
a second connector configured to connect detachably the primary light source module with the light guide path,
wherein the first connector has an access restricting portion including an access restriction cover being configured to inhibit an operation of attaching or detaching the light guide path to or from the light conversion unit such that attachment and detachment of the first connector is more difficult than attachment and detachment of the second connector, the access restriction cover covering at least a portion of an outer peripheral surface of the first connector such that a first end of the access restriction cover engages with a proximal most end of the first connector and a second end of the access restriction cover engages with a distal most end of the first connector, the first and second ends of the access restriction cover being separated by a length in a longitudinal direction of the first connector.

2. The apparatus according to claim 1, wherein
access restriction of the access restricting cover is canceled by a predetermined access restriction canceling operation and an attaching/detaching operation between the light guide path and the light conversion unit is enabled.

3. The apparatus according to claim 2, wherein the first connector is provided at one end portion of the light guide path, and the second connector is provided at the other end portion of the light guide path.

4. The apparatus according to claim 3, wherein
the light guide path is an optical fiber,
the light conversion module has a light conversion unit side optical fiber having one end connected to the light conversion unit, and
the access restricting cover of the first connector is formed out of a sleeve configured to be fitted onto a connecting portion between a ferrule fixed to a connection end of the optical fiber which is the light guide path and a ferrule fixed to a connection end of the light conversion unit side optical fiber.

5. The apparatus according to claim 2, wherein the access restricting cover has a physical structure configured to inhibit physically an operation of attaching/detaching the first connector.

6. The apparatus according to claim 5, wherein the physical structure cancels the access restriction of the first connector by an access restriction canceling operation using a tool.

7. The apparatus according to claim 6, wherein
the tool for the access restriction canceling operation is a special tool having a special distal end shape, and
the access restricting cover has a fitting structure with a special shape associated with the distal end shape of the special tool.

8. The apparatus according to claim 2, wherein
the access restriction cover is configured to cover a substantially entire outer peripheral surface of the first connector in a state that the first connector is connected, and
the predetermined access restriction canceling operation is carried out by an operation of removing the cover.

9. The apparatus according to claim 8, wherein the access restriction cover is a cover member having at least one of waterproof properties, heat resisting properties, and impact resisting properties.

10. The apparatus according to claim 2, wherein the access restricting cover includes a warning display portion that is provided near the access restricting cover of the first connector.

11. The apparatus according to claim 1, wherein an attached function of the second connector is different from that of the first connector.

12. The apparatus according to claim 11, wherein
the first connector has a higher level of access restriction than that of the second connector, and
attachment and detachment of the second connector are more easily enabled than the first connector.

13. The apparatus according to claim 11, wherein
the second connector has a higher level of safety than the first connector, and
the second connector has a smaller risk of leakage of the primary light to the outside than the first connector when a connecting operation error occurs.

14. The apparatus according to claim 11, wherein an area of a section of the second connector taken along a plane orthogonal to a light guiding direction of the primary light is larger than that of the first connector.

15. The apparatus according to claim 11, wherein
each of the first and second connectors has a connecting function of connecting light guide paths, and
a distance between light guide paths adjacent to each other in the light guide paths in the first connector is configured to be smaller than that in the second connector.

16. The apparatus according to claim 11, wherein
the first connector and the second connector has a waterproof function, and
the waterproof function of the first connector is configured to have a higher level than that of the second connector.

17. The apparatus according to claim 11, wherein
the first connector has resistance against repetition of the attachment and detachment that is different from that of the second connector, and
the second connector is configured to have higher abrasion resisting properties in a contact region that is brought into contact and slid at the time of the attaching/detaching operation than the first connector.

18. The apparatus according to claim 1, wherein the light guide path includes a light guide member having flexibility, and the first connector is provided in the light guide member or provided at an end of the light guide member.

19. The apparatus according to claim 18, wherein the first connector and the second connector are provided on both sides to sandwich the light guide member.

20. The apparatus according to claim 19, wherein the first connector is provided on the light conversion unit side of the light guide member, and the second connector is provided on the primary light source side of the light guide member.

21. The apparatus according to claim 1, wherein the access restriction cover is configured to cover the first connector and its periphery.

22. The apparatus according to claim 1, wherein the access restriction cover is configured to cover from the light conversion module to the light guide path.

23. The light source apparatus according to claim 1, wherein, in a state that the first connector is connected, the access restriction cover is configured to cover at least one of:
substantially an entire outer peripheral surface in a radial direction of the first connector, and
substantially an entire outer peripheral surface in an axial direction of the first connector.

24. The light source apparatus according to claim 1, wherein
the first connector comprises a distal end side connector and a proximal end side connector which are detachable to each other,
the access restriction cover is configured to cover the distal end side connector and the proximal end side connector from an outer peripheral side; and
the second connector does not include an access restriction cover to inhibit an operation of attaching or detaching the primary light source to or from the light guide path.

25. The light source apparatus according to claim 1, wherein
the access restriction cover is configured to cover a substantially entire outer peripheral surface of the first connector in a state that the first connector is connected, and the light conversion module is detached with the light guide path only when an access restriction canceling operation is carried out by an operation of removing the access restriction cover.

26. A light source apparatus comprising:
a primary light source module including a primary light source configured to emit primary light;
a light conversion module including a light conversion unit configured to convert optical properties of the primary light emitted from the primary light source and to generate secondary light;
a light guide path, arranged between the primary light source module and the light conversion module, configured to guide the primary light emitted from the primary light source to the light conversion module from the primary light source module;
a first connector configured to connect detachably the light conversion module with the light guide path; and
a second connector configured to connect detachably the primary light source module with the light guide path,
wherein the first connector has an access restricting portion,
the second connector has a predetermined restricting portion different from the access restricting portion; and
the access restriction portion being configured to inhibit an operation of attaching or detaching the light guide path to or from the light conversion unit such that attachment and detachment of the first connector is more difficult than attachment and detachment of the second connector, the access restriction portion covering at least a portion of an outer peripheral surface of the first connector such that a first end of the access restriction portion engages with a proximal most end of the first connector and a second end of the access restriction portion engages with a distal most end of the first connector, the first and second ends of the access restriction portion being separated by a length in a longitudinal direction of the first connector.

27. The apparatus according to claim 26, wherein the predetermined restricting portion is at least one of a safety structure, a waterproof mechanism and an abrasion resistant mechanism.

28. The apparatus according to claim 27, wherein the safety structure comprises one of a shutter and an interlock.

29. The apparatus according to claim 27, wherein the abrasion resistant mechanism comprises a high abrasion resistance material in a contact region.

30. The apparatus according to claim 26, wherein the predetermined restricting portion is an access restriction portion such that:
the first connector has a higher level of access restriction than that of the second connector, and
attachment and detachment of the second connector are more easily enabled than the first connector.

31. The apparatus according to claim 26, wherein the predetermined restricting portion is a safety restriction portion such that:
the second connector has a higher level of safety than the first connector; and
the second connector has a smaller risk of leakage of the primary light to the outside than the first connector when a connecting operation error occurs.

32. The apparatus according to claim 26, wherein the predetermined restricting portion is a waterproof restriction portion such the first connector and the second connector has a waterproof function; and the waterproof function of the first connector is configured to have a higher level than that of the second connector.

33. The apparatus according to claim 26, wherein
the predetermined restricting portion is a resistance restriction portion such that:
the first connector has resistance against repetition of the attachment and detachment that is different from that of the second connector; and
the second connector is configured to have higher abrasion resisting properties in a contact region that is brought into contact and slid at the time of the attaching/detaching operation than the first connector.

34. The light source apparatus according to claim 26, wherein
the first connector comprises a distal end side connector and a proximal end side connector which are detachable to each other,
the access restriction cover is configured to cover the distal end side connector and the proximal end side connector from an outer peripheral side; and
the second connector does not include an access restriction cover for inhibiting an operation of attaching or detaching the primary light source to or from the light guide path.

35. A light source apparatus comprising:
a primary light source module including a primary light source configured to emit primary light;
a light conversion module including a light conversion unit configured to convert optical properties of the primary light emitted from the primary light source and to generate secondary light;
a light guide path, arranged between the primary light source module and the light conversion module, configured to guide the primary light emitted from the primary light source to the light conversion module from the primary light source module;
a first connector configured to connect detachably the light conversion module with the light guide path; and
a second connector configured to connect detachably the primary light source module with the light guide path,
wherein the first connector has an access restricting portion and the second connector is configured such that it does not have access restriction; and
the access restriction portion being configured to inhibit an operation of attaching or detaching the light guide path to or from the light conversion unit such that attachment and detachment of the first connector is more difficult than attachment and detachment of the second connector, the access restriction portion covering at least a portion of an outer peripheral surface of the first connector such that a first end of the access restriction portion engages with a proximal most end of the first connector and a second end of the access restriction portion engages with a distal most end of the first connector, the first and second ends of the access restriction portion being separated by a length in a longitudinal direction of the first connector.

36. The apparatus according to claim 35, wherein the access restricting portion is an access restriction cover.

37. The light source apparatus according to claim 35, wherein
the first connector comprises a distal end side connector and a proximal end side connector which are detachable to each other, the access restriction cover is configured to cover the distal end side connector and the proximal end side connector from an outer peripheral side; and the second connector does not include an access restriction cover for inhibiting an operation of attaching or detaching the primary light source to or from the light guide path.

38. An endoscope comprising:

a primary light source module including a primary light source configured to emit primary light; and an insertion portion having a protection cover for covering an outer periphery of the insertion portion, an interior of the insertion portion including:

a light conversion module including a light conversion unit configured to convert optical properties of the primary light emitted from the primary light source and to generate secondary light;

a light guide path, arranged between the primary light source module and the light conversion module, configured to guide the primary light emitted from the primary light source to the light conversion module from the primary light source module; and a first connector configured to connect detachably the light conversion module with the light guide path, wherein the first connector has an access restricting portion, the light guide path includes a light guide member having flexibility, and the first connector is provided in the light guide path or provided at an end of the light guide member;

the access restriction portion being configured to inhibit an operation of attaching or detaching the light guide path to or from the light conversion unit, the access restriction portion covering a substantially entire outer peripheral surface of the first connector such that a first end of the access restriction portion engages with a proximal most end of the first connector and a second end of the access restriction portion engages with a distal most end of the first connector, the first and second ends of the access restriction portion being separated by a length in a longitudinal direction of the first connector; and the protection cover comprises the access restriction portion.

39. The endoscope according to claim 38, further comprising a second connector configured to connect detachably the primary light source module with the light guide path.

40. The endoscope according to claim 38, wherein an area of a section of the second connector taken along a plane orthogonal to a light guiding direction of the primary light is larger than that of the first connector.

41. The endoscope according to claim 38, wherein each of the first and second connectors has a connecting function of connecting light guide paths, and a distance between light guide paths adjacent to each other in the light guide paths in the first connector is configured to be smaller than that in the second connector.

42. The endoscope according to claim 38, wherein the first connector and the second connector are provided on both sides to sandwich the light guide member.

43. The endoscope according to claim 42, wherein the first connector is provided on the light conversion unit side of the light guide member, and the second connector is provided on the primary light source side of the light guide member.

* * * * *